(12) United States Patent
Khedr et al.

(10) Patent No.: US 11,744,869 B1
(45) Date of Patent: Sep. 5, 2023

(54) COMPOSITIONS AND METHODS FOR TREATMENT OF ADDICTION WITHDRAWAL SYMPTOMS

(71) Applicant: KING ABDULAZIZ UNIVERSITY, Jeddah (SA)

(72) Inventors: Alaa Eldin M. Khedr, Jeddah (SA); Maha Ibrahim, Jeddah (SA); Ammar Bayoumi, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 18/150,364

(22) Filed: Jan. 5, 2023

(51) Int. Cl.
| | | |
|---|---|---|
| *A61K 36/71* | (2006.01) | |
| *A61K 35/60* | (2006.01) | |
| *A61P 25/36* | (2006.01) | |
| *A61K 47/10* | (2017.01) | |

(52) U.S. Cl.
CPC .............. *A61K 36/71* (2013.01); *A61K 35/60* (2013.01); *A61K 47/10* (2013.01); *A61P 25/36* (2018.01); *A61K 2236/333* (2013.01)

(58) Field of Classification Search
None
See application file for complete search history.

(56) References Cited

U.S. PATENT DOCUMENTS

| | | | |
|---|---|---|---|
| 11,186,597 B1 * | 11/2021 | Khedr | C07F 9/103 |
| 2008/0089999 A1 * | 4/2008 | Alpern | A23L 33/115 |
| | | | 426/643 |
| 2011/0165262 A1 * | 7/2011 | Al-Sari | A61P 25/30 |
| | | | 514/276 |

FOREIGN PATENT DOCUMENTS

EP 2085089 A1 * 8/2009 ......... A61K 31/6615

OTHER PUBLICATIONS

Ahmad et al. (2013) Asian Pac. J. Trop. Biomed. 3(5): 337-352. (Year: 2013).*
Guedes et al. (2022) Separations 9: 210 (17 pages). (Year: 2022).*
Ma et al. (2019) Journal of Food Quality, Article ID: 2592731. (6 pages). (Year: 2019).*
Murota et al. (2018) Protaglandins, Leukotrienes and Essential Fatty Acids, 139: 40-48. (Year: 2018).*
Shirai et al. (2008) Food Sci. Technol. Res. 14(1): 25-31. (Year: 2008).*

* cited by examiner

*Primary Examiner* — Russell G Fiebig
(74) *Attorney, Agent, or Firm* — WC&F IP

(57) ABSTRACT

Provided herein are formulations composed of fish roe wax extract and *Nigella sativa* oil extract. This oily composition is prepared and used as a treatment for addiction withdrawal symptoms by regulating dopamine and serotonin unbalance in a subject in need thereof. The prepared formulation alleviated the addiction effect of cocaine after daily single dosing of addiction-induced mice.

12 Claims, 4 Drawing Sheets

United States Patent 11,744,869 B1

COMPOSITIONS AND METHODS FOR TREATMENT OF ADDICTION WITHDRAWAL SYMPTOMS

FIELD OF THE INVENTION

The disclosure provides formulations comprising fish roe extract and *Nigella sativa* oil extract. This oily composition is useful for the treatment of drug addiction withdrawal symptoms, such as cocaine addiction withdrawal symptoms.

BACKGROUND

Nicholls et al. summarized the most important governmental agencies in charge of the recommended treatment protocols for opioid and narcotics addiction (1). The guidelines for treating opioid dependence have been developed by many organizations, including the American Society of Interventional Pain Physicians (ASIPP) and the American Psychiatric Association (APA). The National Institute on Drug Abuse (NIDA) is the leading federal agency supporting scientific research on drug use and addiction. The current guidelines comprehensively recommend methadone, buprenorphine, buprenorphine combined with naloxone, and psychosocial therapy as a treatment for opioid addiction. The journey of addiction treatment takes a relatively long time, up to more than a year, to reach full recovery (2, 3). Sometimes side effects occur during therapy due to applying a specific treatment protocol. Therefore, resorting to treatment with natural herbs or natural biological products gives less chance of side effects.

Abdul-Hannan et al. published a comprehensive review of *Nigella sativa* and its phytochemistry, health benefits, pharmacological effects, and safety (4). *Nigella sativa* L. (called black seeds, black cumin) is historically known as a traditional medicinal herb (5). *Nigella sativa* (NS) seeds were used as powder, decoction in hot water, or extract for treating many conditions or diseases, including; respiratory problems, inflammation, mental stress, eczema, and rheumatism (5). It has been reported that NS exerts a protective effect against neuroinflammation (6). The neuroprotection effect has been attributed to the thymoquinone contents of NS (7). NS also has been used as a natural adjuvant product to protect against Alzheimer's disease (8, 9). Further, neurodegeneration and depression have been treated by using *Nigella sativa* extract and its volatile components as dietary supplements (10).

The US patent application 20110165262 to Al-Sari et al., incorporated herein by reference, described the preparation of some mixtures to reduce drug dependence or addiction (11). *Nigella sativa* was described among the herbal constituents as antioxidants that help reduce mental stress and recover from drug dependence. Ma et al., 2019, described an extraction procedure for *Nigella sativa* (NS) seeds using liquid-solid extraction (12). This extraction method considered four factors that affect the extraction rate, including the particle size of the seeds, liquid-seed ratio, extraction time, and temperature (13). This procedure showed a maximum oil recovery of 43.78% after extraction with n-hexane "8 mL for each 1 g powder" at 40° C. for 1.5 h. The maximum % recovery of linoleic acid (C18:2) was 58.1 mg/g. This procedure showed an oily extract with black-colored co-extracted material.

Improved methods for obtaining *Nigella sativa* extract with a high content of natural bioactive entities with minimal coextracted black dye are needed. Improved formulations for treating addiction withdrawal symptoms are also needed.

SUMMARY OF THE INVENTION

Provided herein is a matrix preparation containing oil extract of *Nigella sativa* (NS) seeds and fish roe wax extract. The fish roe extract was combined with the NS oil to synergistically improve psychomotor behavior and mental health, which accelerates anti-addiction and anti-depression effects.

In some embodiments, the fish roe is selected from the group consisting of hamour roe, salmon roe, tuna roe, mosa roe, sevruga sturgeon roe, lump roe, bory roe, and combinations thereof. In some embodiments, the formulation further comprises a solvent, such as polyethylene glycol 200. In some embodiments, the formulation comprises 75-400 mg fish roe wax extract and 600-925 mg *Nigella sativa* seed oil extract. In some embodiments, the *Nigella sativa* seed oil extract was obtained using an extraction solvent comprising chloroform and methanol. In some embodiments, the chloroform and methanol are at a ratio of 2:1.

Another aspect of the disclosure provides a method for increasing dopamine and serotonin levels in a subject in need thereof, comprising administering to the subject a formulation as described herein. In some embodiments, the subject suffers from addiction withdrawal symptoms. In some embodiments, the subject suffers from cocaine withdrawal symptoms.

Additional features and advantages of the present invention will be set forth in the description of disclosure that follows, and in part, will be apparent from the description of may be learned by practice of the disclosure. The disclosure will be realized and attained by the compositions and methods particularly pointed out in the written description and claims hereof.

DETAILED DESCRIPTION

Figure 1:
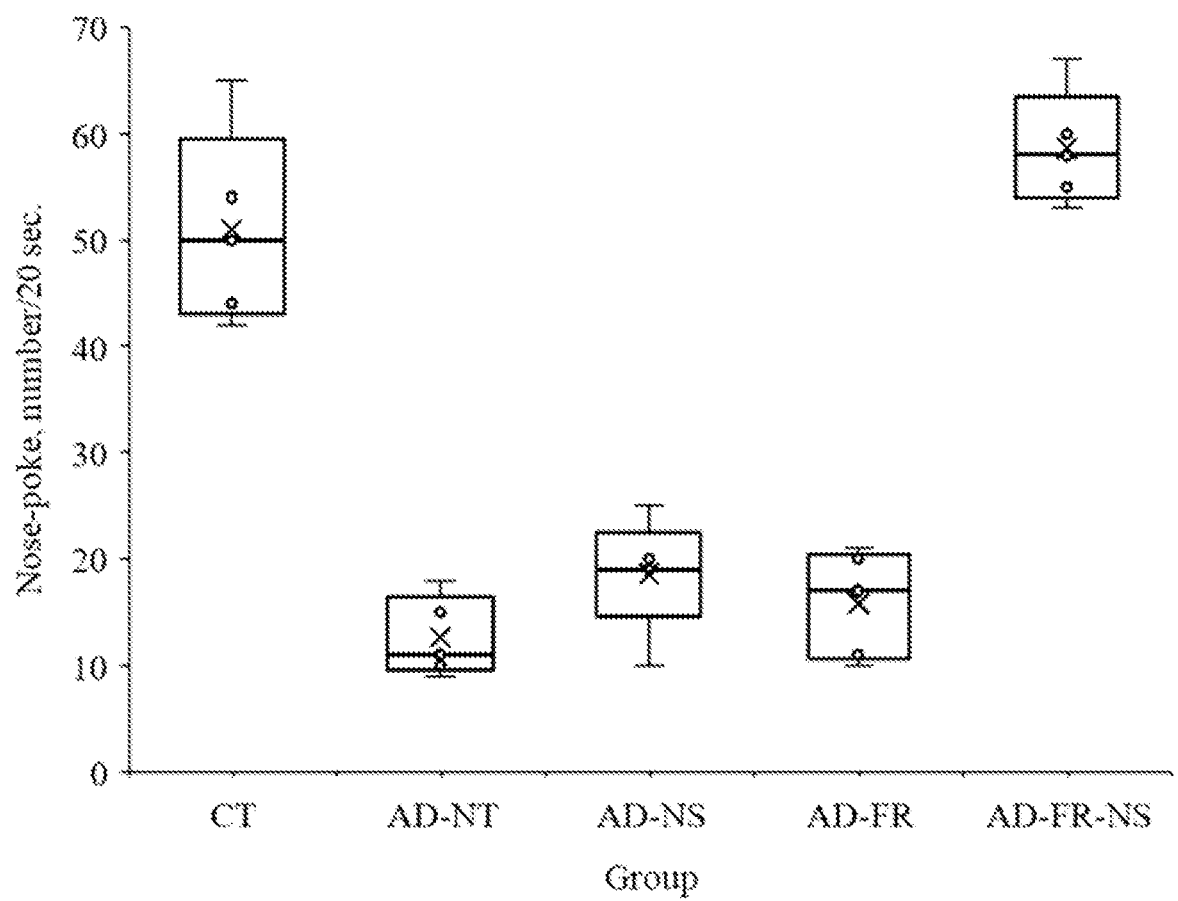
FIG. 1. Average test results of nose-pokes on the control group, addict group at day 7, and after day 7 of treatment with NS, FR, and FR-NS mix.

The preferred embodiments of the present disclosure are directed toward a formulation comprising fish roe wax extract mixed with *Nigella sativa* seed oil extract. The formulation contains natural components that are useful for the treatment of addiction withdrawal symptoms, such as cocaine addiction withdrawal symptoms. In some embodiments, the fish roe extract and the *Nigella sativa* seed oil extract are the sole active ingredients in the formulation, i.e. the formulation does not contain any other agents useful for treating addiction or addiction withdrawal symptoms. In some embodiments, the formulation does not contain any other plant extracts.

Methods for obtaining a fish roe extract are described in U.S. Pat. No. 11,186,597 incorporated herein by reference.

The method may comprise steps of collecting and freezing fish roe, drying and grinding the fish roe into a powder form, blending the fish roe with a solvent under conditions such that one or more phospholipids are preferentially extracted to form bioactive phospholipids and biological residue materials, and drying to produce isolated phospholipids under vacuum. The method includes a direct extract-and-dry process, which does not include a step of washing, particularly a washing step with a water-containing solution or by adding the aqueous solution to dilute the extraction solvent.

Any stages or types of fish roe, such as mature fish roe or immature fish roe, may be contemplated for the extraction method. In particular, hamour roe, salmon roe, tuna roe, mosa roe, sevruga sturgeon roe, lump roe, bory roe, or combinations thereof may be used.

The fish roe extract may contain bioactive fatty acids such as omega-3 fatty acids. Non-limiting examples of omega-3 fatty acids include $\Delta$-5,8,11,14,17-eicosapentaenoic acid (EPA), $\Delta$-4,7,10,13,16,19-docosahexanoic acid (DHA) and $\Delta$-7,10,13,16,19-docosapentanoic acid (n-3 DPA). In some embodiments, the extracted omega-3 fatty acids, including EPA and DHA that are bound to phospholipids (i.e., phospholipid molecule having an omega-3 fatty acid residue at the sn1 position, the sn2 position or both) and has a superior bioavailability for the dietary supplement use. In some embodiments, the bioactive fatty acid and bioactive residue materials of the extracts may comprise 1-99% of omega-3 fatty acids.

The term "phospholipid" as used herein refers to a glycerol phosphate with an organic headgroup such as choline, serine, ethanolamine or inositol and either one or two fatty acids esterified to the glycerol backbone. Phospholipids include, but are not limited to, phosphatidylcholine, phosphatidylethanolamine, phosphatidylserine and phosphatidylinositol as well as corresponding lysophospholipids. The term "phospholipid wax" or "PL wax" refers to a mass of phospholipids that is a solid at room temperature (~23° C.). A PL wax as described herein can have a melting point interval in the range of about 28° C. to about 65° C. Some PL waxes can have a melting point interval in the range of about 28° C. to about 38° C., about 28° C. to about 35° C., about 28° C. to about 34° C., about 35° C. to about 65° C., about 40° C. to about 60° C., about 45° C. to about 55° C., or about 55° C. to about 65° C. Other PL waxes can have a melting point interval in the range of about 50° C. to about 60° C., about 40° C. to about 50° C., about 30° C. to about 40° C., about 30° C. to about 38° C., about 30° C. to about 35° C., or about 30° C. to about 33° C. The melting point interval can be an interval of about 2, about 3, about 4, about 5, about 7, or about 10° C. within one of the recited ranges. The PL wax can be pliable and the solid can be dissolvable in oils such as vegetable or fish oils or *Nigella sativa* seed oil.

*Nigella sativa* seed oil may be obtained by grinding *Nigella sativa* seeds into a fine powder and mixing the powder with an extraction solvent. After centrifugation, the supernatant layer is aspirated and transferred to flask, and the solvent is removed by evaporation to obtain an oily residue.

In preferred embodiments, the extraction solvent comprises a mixture of chloroform and methanol in various volume per volume ratios. In some embodiments, the ratio of chloroform to methanol may be about 3:1 to 1:1 v/v, e.g. about 2:1 v/v. In other embodiments, the solvent may further include other food-safe solvents selected from the group consisting of n-hexane, cyclohexane, liquid propane, acetone, ethyl acetate, and combinations thereof. In some embodiments, the extraction method may further include a supercritical fluid extraction with carbon dioxide. Further, in some embodiments, the extraction method does not include washing of the extract with an aqueous solution or diluting of the extraction solvents with water during purification.

The combined formulation may be prepared by allowing the fish roe and *Nigella sativa* seed oil extracts to melt at room temperature and then combining the two extracts. In some embodiments, the formulation comprises 75-400 mg fish roe wax extract and 600-925 mg *Nigella sativa* seed oil extract for a total dose of 1000 mg. For example, the formulation may comprise 75 mg fish roe wax extract and 925 mg *Nigella sativa* seed oil extract, or 150 mg fish roe wax extract and 850 mg *Nigella sativa* seed oil extract, or 225 mg fish roe wax extract and 775 mg *Nigella sativa* seed oil extract, or 300 mg fish roe wax extract and 700 mg *Nigella sativa* seed oil extract.

In some embodiments, the formulation further comprises a solvent, such as polyethylene glycol 200. In some embodiments, the formulations described herein may further comprise other agents, such as flavoring agents, sweeteners, emulsifiers, nutritional supplements, and deodorants.

The methods and uses described herein may further include treating a subject in need thereof, comprising the steps of administering the formulation in an oral delivery vehicle, food product, nutritional supplement, dietary supplement, or functional food comprising the formulation to the subject. In some embodiments, the administration is oral, topical, parenteral, enteral, transdermal, intradermal, intraocular, intravitreal, sublingual, or intravaginal, and may preferably comprise an effective amount of the composition.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

The formulations described herein are useful for regulating dopamine and serotonin unbalance in a subject, e.g. by increasing dopamine and serotonin levels. For example, the unbalance may be due to withdrawal from a substance abuse disorder, such as cocaine addiction. The subject may have been addicted to any drug of abuse, e.g. alcohol, nicotine, steroids, stimulants, performance-enhancers, hallucinogens, opioids, narcotics, etc.

Those of ordinary skill in the art will appreciate that substance abuse often involves symptoms of physical and/or psychological "dependence." Also, when the substance of abuse is withdrawn from a dependent individual, the individual often develops certain symptoms including sleep and mood disturbance and intense craving of the substance of abuse, known as "withdrawal." The methods described herein encompass treatment of substance abuse itself, dependence, and also of withdrawal.

"Withdrawal" refers to a collection of symptoms that arise when administration of a relevant substance is reduced, delayed, or stopped. The substance-specific symptoms of withdrawal can cause clinically significant distress or impairment in social, occupational or other important areas of functioning, for example. These symptoms are not due to a general medical condition and are not better accounted for by another mental disorder. Withdrawal usually, but not necessarily, is associated with substance dependence. In some embodiments, treatment with a formulation as described herein reduces at least one symptom of withdrawal in a patient. In some embodiments, withdrawal symptoms include for example and without limitation apathy, irritability, recklessness, poor judgment, compulsion, aggression, anger, substance craving, mood disorders, and sleep disorders. In some embodiments, treatment with a formulation as described herein reduces the substance craving induced by a stressful event in a patient.

Cocaine abuse and dependence can cause cognitive, behavioral, and physiological symptoms. Symptoms of cocaine abuse and dependence can include varying degrees of attention deficit hyperactivity disorder and euphoria; increased energy, excitement, and sociability; less hunger and fatigue; a marked feeling of physical and mental strength; dysphoria; decreased sensation of pain; and craving for cocaine. Respiratory effects include symptoms such as bronchitis, shortness of breath, and chest pain, and cardiovascular effects include symptoms such as heart palpitations, arrhythmia, cardiomyopathy, and heart attacks. Symptoms also include dilated pupils, nausea, vomiting, headache, vertigo, anxiety, dizziness, psychosis, and confusion. Administration of cocaine through snorting or sniffing can result in ear, nose, and throat effects including nasal irritation, nasal crusting, recurrent nosebleeds, nasal stuffiness, and facial pain. In some embodiments, treatment with a formulation as described herein reduces at least one symptom of cocaine abuse and dependence in a patient.

Cocaine withdrawal symptoms can include a fatigue, lack of pleasure, depression, irritability, sleep disorders, increased appetite, psychomotor retardation, agitation, extreme suspicion, and craving for cocaine. In some embodiments, treatment with a formulation as described herein reduces at least one symptom of cocaine withdrawal.

As used herein, the phrase "reduces a symptom" refers to reducing at least one of the frequency and amplitude of a symptom of a condition in a patient. In certain embodiments the patient enters remission and no longer experiences the symptom.

In some embodiments, the formulation is an oily solution or suspension. In some embodiments, the formulation is in a solid dosage form, such as a form selected from the group consisting of a tablet, dragee, capsule, caplet and gelcap.

The formulation may further comprise one or more pharmaceutically acceptable carriers. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

In some embodiments, the formulation is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250, 500, and 1,000 mg of the active ingredient for the symptomatic adjustment of the dosage to the subject to be treated. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4, 5, 6, 7, or more times weekly.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

EXAMPLE

Cocaine is a central nervous system stimulant which leads to a high extracellular level of dopamine and serotonin. The addiction to cocaine and similar drugs leads to cellular disturbance of dopamine and serotonin re-uptake due to disturbance of lipid composition of the neuronal cell membrane. Herein, we describe a preparation that helps in restoring the addict mice to a normal physiological and behavioral status. We published previously the preparation of fish roe (FR) extract with maximum yield that helps in the treatment of mental health problems "Khedr A, Omar A, Method of extracting phospholipids from fish roe, U.S. Pat. No. 11,186,597 B1. Nov. 30, 2021 Nov. 30, 2021". Herein, we show a procedure for the preparation of a formula containing FR extract and oily extract prepared from the seeds of Nigella sativa (NS). The formulation was prepared to contain a normal dose which is prescribed for human use as a natural traditional medicine. The formulation was prepared in the form of a waxy-oily matrix intended for oral administration containing 1000 mg per single dose. The equivalent dose to mice was prepared by using polyethylene glycol 200 as diluent matrix.

This preparation was tested on groups of mice that had been previously rehabilitated for cocaine addiction. The effect of the orally administered FR-NS formula showed a complete recovery from the addiction symptoms. A formula administration for seven subsequent days was enough to alleviate the addiction. The treated groups retained a normal level of dopamine and serotonin in the brain.

TABLE 1

| Abbreviations | |
| --- | --- |
| Letters | Abbreviation of; |
| CT | Control group |
| AD-NT | Addict group - not treated |
| AD-NS | Addict group - treated with NS extract |
| AD-FR | Addict group - treated with FR extract |
| AD-FR-NS | Addict group - treated with a combination of FR and NS extract |

Preparation of Nigella sativa Oil

Three grams of Nigella sativa seeds were ground into a fine powder using an electric grinder. The obtained powder was sieved, and a weight of 1 g was transferred to 15-mL screw-capped test tube. This powder was mixed with 8 mL extraction solvent composed of chloroform:methanol, 1:1, v/v, vortexed for 5 min, sonicated for 45 min, and centrifuged at 5000 rpm for 15 min. The clear supernatant layer was aspirated carefully with a Pasteur pipette, transferred to a pear-shaped flask, and the solvent was removed by evaporation using a rotary evaporator at 30° C. The oily residue was weighed to calculate the % recovery of oil as g %. The oily extract was kept at $-80°$ C. in a brown glass container tightly sealed under nitrogen gas. Other solvent combinations were tried to get the optimal percentage recovery.

Preparation of Fish Roe Wax Extract

The Dried Hamour roe was extracted as described by Khedr et al, incorporated herein by reference (14). The wax extract was kept at $-80°$ C. in a brown glass container tightly sealed under nitrogen gas.

Preparation-FR-NS Solution

The NS oil and FR wax extracts were brought out of the refrigerator and kept at room temperature until melted. A weight of 0.6 g of FR extract was transferred to a 50-mL glass beaker and mixed with 3.4 g of NS oil extract. This mixture contained FR wax and NS oil at a ratio of 1.5:8.5, w/w. The dose intended for human use is equivalent to a total concentration of 1000 mg/dose (about 70 kg body weight). A total weight of 4.0 g of this combination was mixed with 100 mL Polyethylene glycol 200, with the aid of heating over a water bath at 40° C. and swirling. The concentration equals 40.0 mg FR-NS extract in 1 mL of PEG-200.

Preparation-FR Solution

A weight of 0.6 g of FR wax was transferred to a 50-mL glass beaker and mixed with 100 mL Polyethylene glycol 200, with the aid of heating over a water bath at 40° C. and swirling. The concentration is equal to 6.0 mg FR extract in 1 mL of PEG-200.

Preparation-NS Solution

A weight of 3.4 g of NS oil was transferred to a 50-mL glass beaker and mixed with 100 mL Polyethylene glycol 200, with the aid of heating over a water bath at 40° C. and swirling. The concentration is equal to 34.0 mg NS oil in 1 mL of PEG-200. Polyethylene glycol 200 was used as a dilution matrix because it's edible, solubilizes the FR wax and NS oil, and enables oral dosing of this preparation to mice. Dosing: each 1 g of mouse dosed with 0.26 g of the waxy preparation combination FR-NS, FR, or NS preparation, equivalent to 6.5 µL of the PEG-200 solution. The used dose of this preparation ranged from 130-195 µL, equal to 20 to 30 g of total mouse body weight.

Preparation Cocaine Solution

The cocaine solution was prepared by dissolving 150 mg of cocaine sulfate in 100 mL of normal saline solution (0.9% sodium chloride). Dosing: A volume of 200 µL of this solution was given orally to contain 0.3 mg of cocaine sulfate.

Mice

Albino mice were used as experimental models for addiction and testing the anti-addiction effect of the FR-NS prepared combination. Animals were housed and fed with standard meals.

Twenty-five Albino meal mice (initial weight, 20-30 g; Charles River, Wilmington, Mass., USA) were individually housed in a temperature- and humidity-controlled vivarium on a 12:12 reverselight-dark cycle (lights off 0600-1800 hours). Animals received water, standard mice chow (Harlan, Indianapolis, Ind., USA), and libitum throughout the experiment. Albino mice were randomly selected and divided into five groups, 15 mice in each group, as follows:

Group 1 (Negative Control):
  A volume of 1 mL/kg was injected intra-peritoneal (i.p) with normal saline (0.9% sodium chloride, w/v) daily for seven days.
Group 2 "Positive Control Addiction Group":
  The addiction was induced by i.p injection of 0.8 mg/kg of cocaine once daily for seven days.
Group 3 "Addiction and Treatment with the NS Oil Solution":
  Animals were injected (i.p) with 0.8 mg/kg of cocaine once daily for seven days, and at day 8 to 14, the animals were fed orally with NS oil solution, 0.22 mg/g via oral gavage daily for seven days.
Group 4 "Addiction and Treatment with FR Wax Solution":
  Animals were injected (i.p) with 0.8 mg/kg of cocaine once daily for seven days, and at day 8 to 14, the animals were fed orally with FR wax solution; 0.04 mg/g via oral gavage daily for seven days.
Group 5 "Addiction and Treatment with the FR-NS-Combination":
  Animals were injected (i.p) with 0.8 mg/kg of cocaine once daily for seven days, and at day 8 to 14, the animals were fed orally with FR-NS combination; 0.26 mg/g via oral gavage daily for seven days. (FR-NS-combination in PEG-200, 40 mg/mL, each 6.5 µL containing 0.26 mg for 1 g mice).

Pre-Clinical Testing

A nose-Pokes test was conducted. The Nose poking was recorded to evaluate neuronal activity in freely moving for all groups (Prus A J, James.2009) to learn how to respond in the operant boxes (15). All animals began the testing phase by learning the simple nose poke response for seven subsequent days before starting the dosing.

The results of nose-poke were recorded at day 7 for Gr-1 and Gr-2. However, the results of nose-poke of Gr-3 to Gr-5 were recorded at day 15. The nose-poke behavior was counted as an average data within 20 min.

Biochemical Analysis

At day 15 of all groups, mice were sacrificed, and the brain samples were collected from all experimental groups to study the Neurotransmitter Interactions by analyzing Dopamine (Cat #MBS2700357, MyBioSource, San Diego, Calif., USA) and Serotonin (Cat #MBS1691042 MyBioSource, San Diego, Calif., USA). A homogenate sample of mice's brain was either analyzed immediately or kept at −80° C. until analysis. The brain tissue was rinsed in ice-cold phosphate-buffered saline (PBS, 0.02 mol/L, pH 7.0-7.2) to remove excess blood thoroughly and weighed before homogenization. The tissues were minced to small pieces and homogenized in a certain amount of PBS with a glass homogenizer on ice. The resulting suspension was subjected to ultrasonication for 30 min to break the cell membranes. After that, the homogenates were centrifugated for 15 minutes at 1500×g. The supernatant was removed and assayed immediately or left at −80° C. until analysis. Materials for ELISA assay: Dopamine ELISA kit (Cat no. MBS2700357) was purchased from MyBioSource (San Diego, Calif., USA). The Serotonin ELISA kit (Cat no. MBS1691042) was purchased from MyBioSource (San Diego, Calif., USA).

An ELISA method measured the dopamine (DA) level in the brain homogenate (16). This assay employs the competitive inhibition enzyme immunoassay technique. Briefly, a mouse monoclonal antibody specific to DA has been pre-coated onto a microplate. A competitive inhibition reaction was launched between biotin-labeled DA and unlabeled DA (standards or samples) with the pre-coated antibody specific to DA. After incubation, the unbound conjugate is washed off. Next, avidin conjugated to Horseradish Peroxidase (HRP) was added to each microplate well and incubated. The amount of bound HRP conjugate was inversely proportional to the concentration of DA in the sample. After adding 3,3',5,5'-tetramethylbenzidine (TMB) substrate solution, the intensity of color developed was inversely proportional to the concentration of DA in the sample.

Serotonin (ST) was determined by an ELISA kit (17). The plate has been pre-coated with mouse ST antibody. ST in the sample was added and bound to antibodies coated on the wells. And then, a second biotinylated mouse ST antibody was added and bound to ST in the sample. Then streptavidin-HRP conjugate was added and bound to the biotinylated ST antibody. After incubation, unbound streptavidin-HRP was washed away during a washing step. A substrate solution was then added, and color developed in proportion to the amount of mouse ST antibody. The enzyme color reaction was terminated by adding an acidic stop solution, and absorbance was measured at 450 nm.

Results and Discussion

Cocaine addiction seriously affects the nervous system, and lipid composition of the cellular membrane makes the treatment a big challenge, and the chance of relapse is high. It has been reported that cocaine exposure resulted in a severe alteration of the lipid composition of the rat's brain [18]. The dysregulation of the brain membrane lipids in correlation to exposure to psychostimulant drugs has been reviewed [19]. The exposure of animals to cocaine or heroin has been studied and showed an alteration of the phospholipid metabolism in a brain region-dependent manner [20, 21]. This metabolic dysregulation has been attributed to the altered activity of the phospholipase enzyme because of addiction to cocaine for one week [22, 23]. The cocaine withdrawal symptoms include depression, anxiety, fatigue, vivid, and psychomotor retardation (18, 19).

This Example described a preparation that contains two food supplants: fish roe extract and *Nigella sativa* oil extract. Fish roe is a rich food supplement in phospholipids that help regenerate damaged neuron cells. The powdered NS was preferably extracted with $CHCl_3$:Et-OH:isopropanol, 2:1: 0.5, v/v, to minimize the incidence of residual solvent toxicity since this solvent mix showed a % recovery indifferent with Bligh and Dyer procedure (Table 2) (20). Table 2 showed that the extraction solvent No. 4 is preferred because it could be volatilized easily while minimizing the loss of volatile active materials, including thymoquinone. The precision of extraction using solvent mix 4 was more advantageous than other solvents tried.

TABLE 2

The percentage recovery of NS oil from the fine powder of NS seeds using different solvents.

| Solvent No | Solvent, 8 mL for 1 g powder | Solvent ratio | Amount as mg out of 1 g | Recovery, g % ± SD |
| --- | --- | --- | --- | --- |
| 1 | Ethanol | N/A | 283 | 28.3 ± 3.65 |
| 2 | Ethanol:isopropanol | 7:1 | 289 | 28.9 ± 2.88 |
| 3 | $CHCl_3$:Et-OH:isopropanol | 2:1:0.5 | 301 | 30.1 ± 1.83 |
| 4 | $CHCl_3$:Me-OH | 2:1 | 302 | 30.2 ± 1.77 |
| | | | | (20) |

The prepared formula containing 15% FR wax and 85% NS oil extract was intended to help in the safe withdrawal of cocaine addiction. The effect of the formulation prepared was tested by monitoring the nose-poke neuronal activity and measuring the level of dopamine and serotonin in the brain. The mice group 1 was used as control; group 2 received cocaine for seven days, left without treatment for seven days and tested on day 15. Groups 3, 4, and 5 were dosed with cocaine for the first seven days, and the dosing was stopped, followed by dosing with either FR extract, NS oil extract, or the prepared FR-NS composite for another seven days and tested on day 15.

As shown in FIG. 1, the recorded data of the Nose pokes test showed that the addict-like mice exhibited reduced neuronal activity compared to the cocaine-negative controls during the first week of abstinence. Also, the cocaine-addicted groups treated with either NS oil or FR wax showed significantly reduced neural activity compared to cocaine-negative controls and combination-treated groups. In contrast, the cocaine-experienced addict group showed an insignificant difference in the neuronal activity of the Nos-Poke test, matching the control group (FIG. 1).

Figure 2:
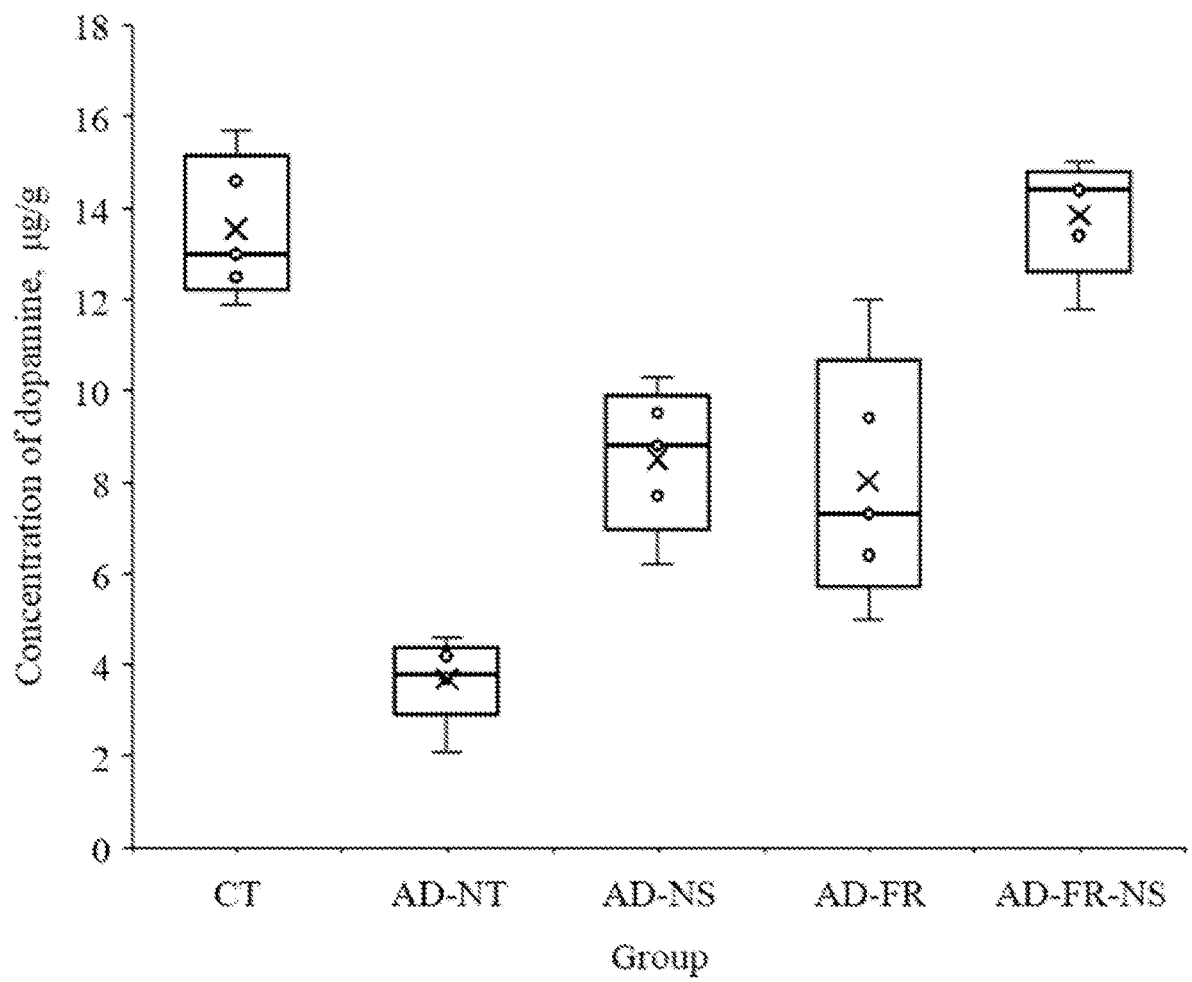
FIG. 2. Average dopamine concentration in the brain homogenates of five groups of mice.

The brain level of dopamine in Gr-2 to Gr-4 was significantly lower, matching the control group (Gr-1). The level of DA in the brain homogenate of both Gr-3 and Gr-4 (addiction treated with NS oil, and FR wax, respectively) was still lower than the control group but higher than the untreated addict Gr-2 (FIG. 2). The addict Gr-5 treated with the FR-NS formula showed a brain-DA level of approximately close to 13.5 µg/mL (Table 3). The treated Gr-5 with the FR-NS formula could retain the normal level of DA in the Brain. That leads to the fact that dysregulated neuronal cell membrane was repaired within seven days with no side effects.

TABLE 3

Average concentration of dopamine and serotonin in mice-brain homogenate in addition to the nose-poke results. p-Values calculated at probability ± 0.05, n = 15 of each group.

|  | Name | Concentration µg/mL ± SD | p-value | * |
|---|---|---|---|---|
| Dopamine | Not addict (control) | 13.54 ± 1.57 | — | — |
|  | Addict, not treated | 3.68 ± 0.95 | 0.00 | ↓ |
|  | Addict, treated with NS | 8.50 ± 1.61 | 0.01 | ↓ |
|  | Addict, treated with FR | 8.02 ± 2.73 | 0.01 | ↓ |
|  | Addict, treated with FR-NS | 13.84 ± 1.28 | 0.24 | — |
| Serotonin | Not addict (control) | 62.58 ± 9.05 | — | — |
|  | Addict, not treated | 9.28 ± 1.04 | 0.00 | ↓ |
|  | Addict, treated with NS | 13.48 ± 2.32 | 0.01 | ↓ |
|  | Addict, treated with FR | 14.54 ± 2.59 | 0.00 | ↓ |
|  | Addict, treated with FR-NS | 58.48 ± 9.83 | 0.56 | — |
| Nose-Poke | Not addict (control) | 51.00 ± 9.17 | — | — |
|  | Addict, not treated | 12.60 ± 3.78 | 0.00 | ↓ |
|  | Addict, treated with NS | 18.60 ± 5.41 | 0.00 | ↓ |
|  | Addict, treated with FR | 15.80 ± 5.07 | 0.00 | ↓ |
|  | Addict, treated with FR-NS | 58.60 ± 5.41 | 0.33 | — |

*Significant increase (↑) or decrease (↓).

Figure 3:
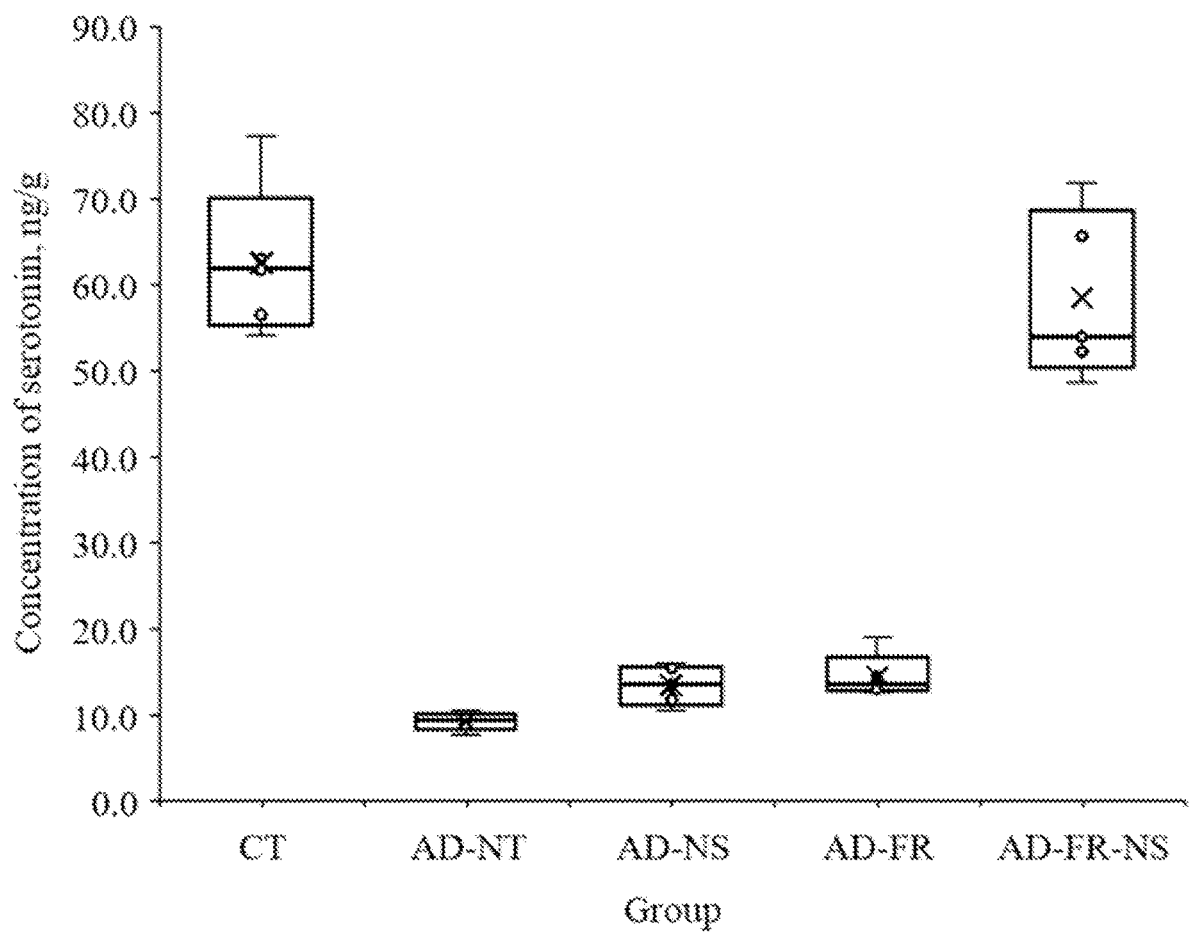
FIG. 3. Average serotonin concentration in the brain homogenate of five groups of mice.

Also, the brain level of serotonin in Gr-2 to Gr-4 was significantly lower, matching with the control group (Gr-1). The level of SE in the brain homogenate of both Gr-3 and Gr-4 (addiction treated with NS oil, and FR wax, respectively) was still lower than the control group but higher than the untreated addict Gr-2 (FIG. 3). The addict Gr-5 treated with the FR-NS formula showed a brain-SE level of approximately close to 60±2 µg/mL (Table 3). The treated Gr-5 with the FR-NS formula could retain the normal level of serotonin in the brain. That leads to the fact that dysregulated neuronal cell membrane was repaired within seven days with no side effects.

Figure 4:
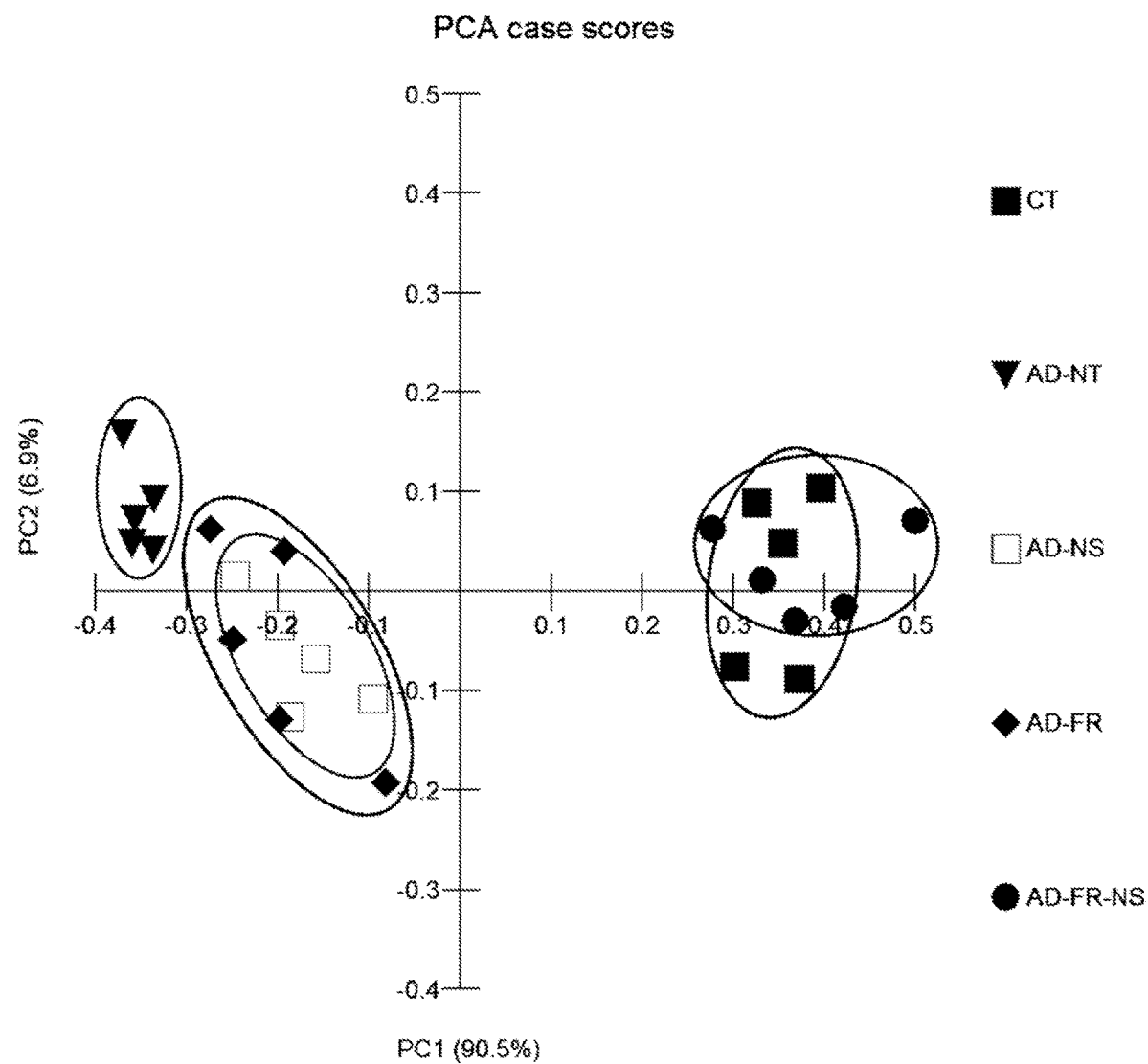
FIG. 4. Principal Component Analysis (PCA), PC1 vs. PC2. Five groups versus three variable parameters.

The score plot shows a matrix similarity between the control group and the addict group treated with the FR-NS combination. The clusters corresponding to the addict-non-treated group and the addict group treated with FR or NS were separated from the control group (FIG. 4).

Withdrawal symptoms can include anxiety, irritability, and depression. These symptoms are caused by the sudden decrease in serotonin and dopamine levels in the brain, which plays a role in regulating mood, so low levels can lead to feelings of sadness and anxiety. That correlated with neuronal activity results. According to our output, the combination treatment can fix dopamine and serotonin unbalance in a record time during the withdrawal symptoms, which contributes to solving the problems and symptoms of withdrawal symptoms and their complications.

REFERENCES

1. Nicholls L, Bragaw L, Ruetsch C. Opioid dependence treatment and guidelines. Journal of managed care pharmacy: JMCP. 2010 February; 16(1 Suppl B):S14-21. PubMed PMID: 20146550. Epub 2010 Feb. 12. eng.
2. Park-Lee E, Lipari R N, Hedden S L, Kroutil L A, Porter J D. Receipt of Services for Substance Use and Mental Health Issues Among Adults: Results from the 2016 National Survey on Drug Use and Health. CBHSQ Data Review. Rockville (Md.): Substance Abuse and Mental Health Services Administration (US); 2012. p. 1-35.
3. Volkow N D, Chang L, Wang G J, Fowler J S, Franceschi D, Sedler M, et al. Loss of dopamine transporters in methamphetamine abusers recovers with protracted abstinence. The Journal of neuroscience: the official journal of the Society for Neuroscience. 2001 Dec. 1; 21(23):9414-8. PubMed PMID: 11717374. Pubmed Central PMCID: PMC6763886. Epub 2001 Nov. 22. eng.
4. Hannan M A, Rahman M A, Sohag A A M, Uddin M J, Dash R, Sikder M H, et al. Black Cumin (*Nigella sativa* L.): A Comprehensive Review on Phytochemistry, Health Benefits, Molecular Pharmacology, and Safety. Nutrients. 2021; 13(6):1784. PubMed PMID: doi:10.3390/nu13061784.
5. Chaudhry Z, Khera R A, Hanif M A, Ayub M A, Sumrra S H. Chapter 13—Cumin. In: Hanif M A, Nawaz H, Khan M M, Byrne H J, editors. Medicinal Plants of South Asia: Elsevier 2020. p. 165-78.
6. Dash R, Mitra S, Ali C M, Oktaviani F D, Hannan A M, Choi M S, et al. Phytosterols: Targeting Neuroinflammation in Neurodegeneration. Current Pharmaceutical Design. 2021; 27(3):383-401.
7. Dash R, Jahan I, Ali M C, Mitra S, Munni Y A, Timalsina B, et al. Potential roles of natural products in the targeting of proteinopathic neurodegenerative diseases. Neurochemistry international. 2021 May; 145:105011. PubMed PMID: 33711400. Epub 2021 Mar. 13. eng.
8. Cascella M, Bimonte S, Barbieri A, Del Vecchio V, Muzio M R, Vitale A, et al. Dissecting the Potential Roles of *Nigella sativa* and Its Constituent Thymoquinone on the Prevention and on the Progression of Alzheimer's Disease. Frontiers in aging neuroscience. 2018; 10:16. PubMed PMID: 29479315. Pubmed Central PMCID: PMC5811465. Epub 2018 Feb. 27. eng.
9. Rahman M A, Rahman M H, Biswas P, Hossain M S, Islam R, Hannan M A, et al. Potential Therapeutic Role of Phytochemicals to Mitigate Mitochondrial Dysfunctions in Alzheimer's Disease. Antioxidants. 2021; 10(1):23. PubMed PMID: doi:10.3390/antiox10010023.
10. Mezger W, inventor Nigella extracts for the treatment of disorders connected to impaired or imbalanced neurotransmission EP 2 289 529 A1, 2010.

11. Al-Sari M, Al-Dabooni R, Jameel Y, inventors Reducing drug dependence or addiction patent US20110165262A1. Jul. 7, 2011.
12. Ma C, Liu C, Ahmed A F, Niu Y, Kang W. Optimum Extraction Technology for the Seed Oil of *Nigella sativa* L. Journal of Food Quality. 2019 2019 Jul. 2; 2019:2592731.
13. Kadam D, Lele S S. Extraction, characterization and bioactive properties of *Nigella sativa* seedcake. Journal of food science and technology. 2017 November; 54(12):3936-47. PubMed PMID: 29085136. Pubmed Central PMCID: PMC5643810. Epub 2017 Nov. 1. eng.
14. Khedr A, Omar A, inventors Method of extracting phospholipids from fish roe patent U.S. Pat. No. 11,186,597 B1. Nov. 30, 2021 Nov. 30, 2021.
15. Prus A J, James J R, Rosecrans J A. Frontiers in Neuroscience, Conditioned Place Preference. In: Buccafusco J J, editor. Methods of Behavior Analysis in Neuroscience. Boca Raton (FL): CRC Press/Taylor & Francis, Copyright © 2009, Taylor & Francis Group, LLC.; 2009.
16. MyBiosource.com. DA elisa kit: General Dopamine (DA) ELISA Kit. Available at: mybiosource.com/general-elisa-kits/dopamine-da/2700357.
17. ST elisa kit: Mouse Serotonin, ST ELISA Kit. Available at: mybiosource.com/mouse-elisa-kits/serotonin-st/1601042.
18. Samuel B. Guze. Diagnostic and Statistical Manual of Mental Disorders, 4th ed. (DSM-IV). American Journal of Psychiatry. 1995; 152(8):1228-.
19. Sofuoglu M, Dudish-Poulsen S, Poling J, Mooney M, Hatsukami D K. The effect of individual cocaine withdrawal symptoms on outcomes in cocaine users. Addictive Behaviors. 2005 2005 Jul. 1; 30(6):1125-34.
20. Bligh E G, Dyer W J. A rapid method of total lipid extraction and purification. Canadian journal of biochemistry and physiology. 1959 August; 37(8):911-7. PubMed PMID: 13671378. Epub 1959 Aug. 1. eng.

What is claimed is:

1. A formulation formulated to treat drug addiction withdrawal symptoms, comprising a therapeutically effective amount of:

phospholipid wax extracted from fish roe; and

*Nigella sativa* seed oil extract, wherein the phospholipid wax and the *Nigella sativa* seed oil extract are present in the formulation at a ratio of 1.5:8.5, w/w, and wherein the formulation is a solid dosage form selected from the group consisting of a tablet, a capsule, a caplet and a gelcap.

2. The formulation of claim 1, wherein the fish roe is selected from the group consisting of hamour roe, salmon roe, tuna roe, mosa roe, sevruga sturgeon roe, lump roe, bory roe, and combinations thereof.

3. The formulation of claim 1, wherein the fish roe is hamour roe.

4. The formulation of claim 1, further comprising a solvent.

5. The formulation of claim 4, wherein the solvent is polyethylene glycol 200.

6. The formulation of claim 1, wherein the formulation 75-400 mg fish roe wax extract and 600-925 mg *Nigella sativa* seed oil extract.

7. The formulation of claim 1, wherein the formulation comprises 75 mg fish roe wax extract and 925 mg *Nigella sativa* seed oil extract.

8. The formulation of claim 1, wherein the formulation comprises 150 mg fish roe wax extract and 850 mg *Nigella sativa* seed oil extract.

9. The formulation of claim 1, wherein the formulation comprises 225 mg fish roe wax extract and 775 mg *Nigella sativa* seed oil extract.

10. The formulation of claim 1, wherein the formulation comprises 300 mg fish roe wax extract and 700 mg *Nigella sativa* seed oil extract.

11. The formulation of claim 1, wherein the *Nigella sativa* seed oil extract was obtained using an extraction solvent comprising chloroform and methanol.

12. The formulation of claim 11, wherein the chloroform and methanol are at a ratio of 2:1 v/v.

* * * * *